US011039790B2

(12) United States Patent
Crawford et al.

(10) Patent No.: US 11,039,790 B2
(45) Date of Patent: **\*Jun. 22, 2021**

(54) GLUCOSE MONITORING DEVICE IN A PROTECTIVE SMARTPHONE CASE

(71) Applicant: Crawford Capital Investments, LLC, Paradise Valley, AZ (US)

(72) Inventors: Spencer Crawford, Scottsdale, AZ (US); Michael Landis, Gilbert, AZ (US)

(73) Assignee: Crawford Capital Investments, LLC, Paradise Valley, AZ (US)

( \* ) Notice: Subject to any disclaimer, the term of this patent is extended or adjusted under 35 U.S.C. 154(b) by 238 days.

This patent is subject to a terminal disclaimer.

(21) Appl. No.: 15/586,737

(22) Filed: May 4, 2017

(65) Prior Publication Data

US 2017/0231574 A1    Aug. 17, 2017

Related U.S. Application Data

(63) Continuation of application No. 13/717,969, filed on Dec. 18, 2012, now Pat. No. 9,642,563.

(51) Int. Cl.
   *G01N 33/66* (2006.01)
   *G01N 33/48* (2006.01)
   (Continued)

(52) U.S. Cl.
   CPC .......... *A61B 5/6898* (2013.01); *A61B 5/1411* (2013.01); *A61B 5/14532* (2013.01);
   (Continued)

(58) Field of Classification Search
   CPC ........ A61B 5/150412; A61B 5/150503; A61B 5/15105; A61B 5/15186; A61B 5/6898;
   (Continued)

(56) References Cited

U.S. PATENT DOCUMENTS 5,593,390 A   1/1997   Castellano et al.
6,159,424 A   12/2000  Kauhaniemi et al.
(Continued)

FOREIGN PATENT DOCUMENTS

GB    2473807    3/2011

OTHER PUBLICATIONS

Office Action dated Jul. 25, 2014 in U.S. Appl. No. 13/717,969.
(Continued)

*Primary Examiner* — Maureen Wallenhorst
(74) *Attorney, Agent, or Firm* — Snell & Wilmer L.L.P.

(57) ABSTRACT

A smartphone protective cover that houses a glucose monitor, test strips, lancets, a lancet striker, a power source, and a biohazard debris receptacle is presented. According to the preferred embodiment of the invention, the protective covering is configured to include a smartphone adapted glucose monitor and also to accept a smartphone. In the preferred embodiment, the smartphone is removably placed into the protective covering with the glucose monitor connecting to a data receptacle on the smartphone. The protective cover further includes a lancet storage compartment adjacent to a lancet striker having a tension control member and striker release button, a test strip storage compartment, and a biohazard debris receptacle. The lancet storage compartment and test strip storage compartment can be re-Tillable or disposable. A battery is also located in the cover and is electrically connected to the glucose for monitor, thus enabling the monitor to be powered independently of the phone. A method of use is also provided.

1 Claim, 10 Drawing Sheets

(51) Int. Cl.
  *G01N 33/487* (2006.01)
  *A61B 5/00* (2006.01)
  *A61B 5/145* (2006.01)
  *A61B 5/15* (2006.01)
  *A61B 5/151* (2006.01)
  *A61B 5/157* (2006.01)

(52) U.S. Cl.
  CPC .... *A61B 5/150022* (2013.01); *A61B 5/15105* (2013.01); *A61B 5/15113* (2013.01); *A61B 5/15186* (2013.01); *A61B 5/150305* (2013.01); *A61B 5/150358* (2013.01); *A61B 5/150412* (2013.01); *A61B 5/150503* (2013.01); *G01N 33/48785* (2013.01); *A61B 5/157* (2013.01); *A61B 2560/0214* (2013.01); *G01N 33/66* (2013.01); *Y10T 436/144444* (2015.01)

(58) Field of Classification Search
  CPC ............ A61B 5/150358; A61B 5/1411; A61B 5/14532; A61B 5/150022; A61B 5/150305; A61B 5/15113; A61B 5/157; A61B 2560/0214; G01N 33/48; G01N 33/48785; G01N 33/66; Y10T 436/144444
  USPC ..... 436/14, 63, 95, 174; 422/410, 68.1, 547, 422/560, 561, 565, 430; 435/14; 600/347, 365, 583; 220/737
  See application file for complete search history.

(56) References Cited

U.S. PATENT DOCUMENTS

| | | | |
|---|---|---|---|
| 7,722,536 B2 | 5/2010 | Goodnow | |
| 9,642,563 B2* | 5/2017 | Crawford | ......... G01N 33/48785 |
| 2005/0240119 A1 | 10/2005 | Draudt et al. | |
| 2005/0277164 A1 | 12/2005 | Drucker et al. | |
| 2006/0009684 A1 | 1/2006 | Kim | |
| 2006/0089542 A1 | 4/2006 | Sands | |
| 2006/0222567 A1 | 10/2006 | Kloepfer et al. | |
| 2006/0278545 A1* | 12/2006 | Henning | ............. A61M 25/002 206/363 |
| 2008/0020794 A1 | 1/2008 | Garon et al. | |
| 2008/0119705 A1 | 5/2008 | Patel et al. | |
| 2008/0299009 A1 | 12/2008 | Angelides | |
| 2010/0069730 A1 | 3/2010 | Bergstrom | |
| 2010/0198107 A1 | 8/2010 | Groll et al. | |
| 2010/0222648 A1 | 9/2010 | Tan et al. | |
| 2010/0249530 A1 | 9/2010 | Rankers et al. | |
| 2011/0256024 A1 | 10/2011 | Cole et al. | |
| 2011/0266149 A1 | 11/2011 | Say | |
| 2011/0282173 A1 | 11/2011 | Fonduca et al. | |
| 2011/0287528 A1 | 11/2011 | Fem et al. | |
| 2012/0029830 A1 | 2/2012 | Turner et al. | |
| 2012/0330189 A1 | 12/2012 | Shaanan et al. | |
| 2014/0106676 A1 | 4/2014 | Yarger et al. | |
| 2014/0128132 A1 | 5/2014 | Cox, III | |

OTHER PUBLICATIONS

Final Office Action dated Aug. 19, 2014 in U.S. Appl. No. 13/717,969.
Notice of Allowance dated Jun. 10, 2015 in U.S. Appl. No. 13/717,969.
Dolan, Brian, FDA clears AgaMatrix's iPhone glucose meter, MobileHealth News (web page: http://mobilehealthnews.com/15137/fda-clears-agamatrixs-iphone-glucose-meter/), Dec. 7, 2011, 1 page, MobileHealth News, USA.
diabetes.co.uk, iBGStar, Diabetes.co.uk web site (http://www.diabetes.co.uk/blood-glucose-meters/sanofi-aventis-ibgstar.html), date of first publication unknown, 1 page, Diabetes.co.uk, United Kingdom.

* cited by examiner

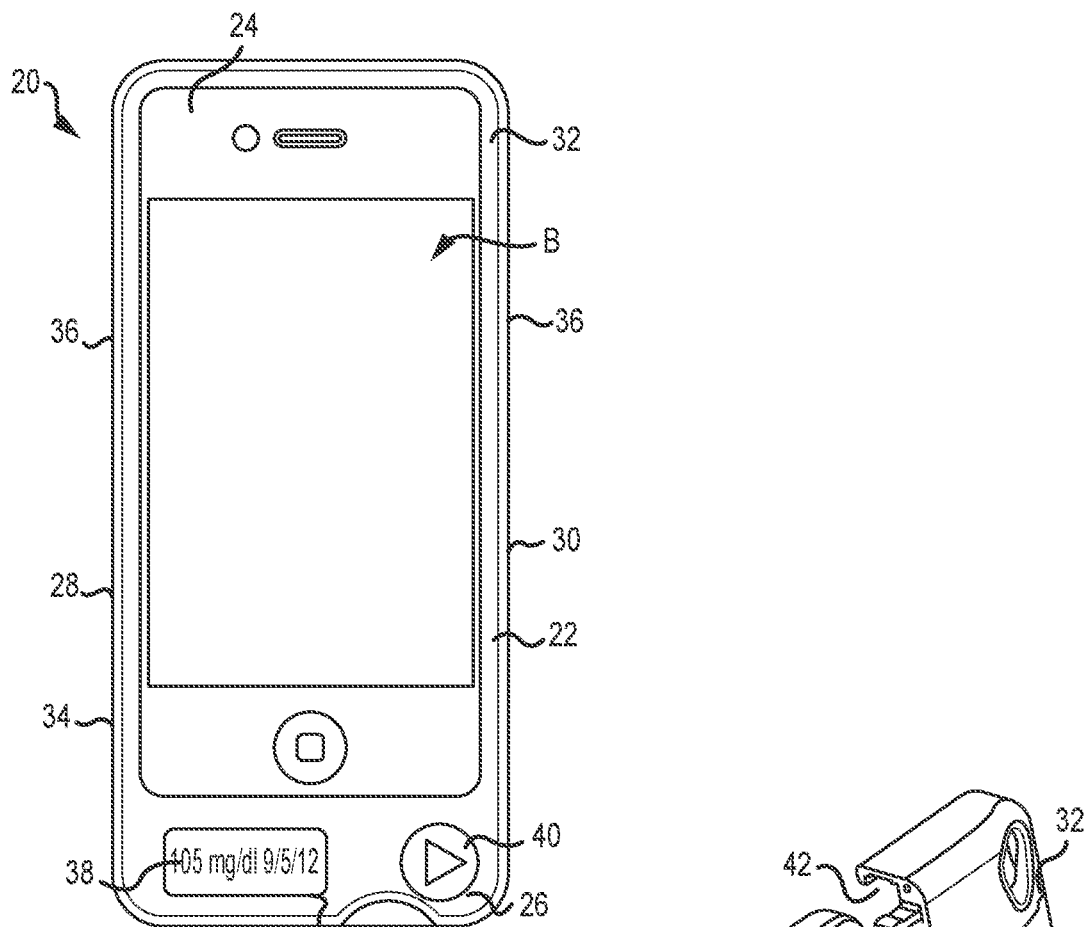
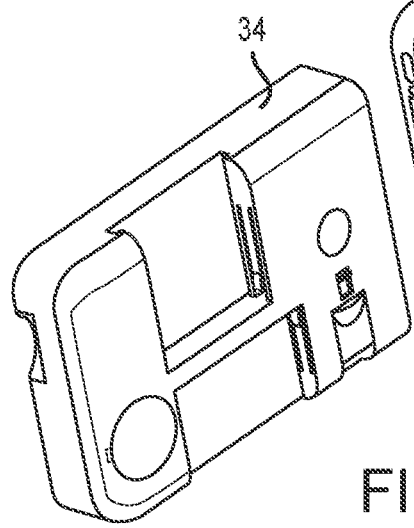
FIG.1
FIG.2

GLUCOSE MONITORING DEVICE IN A PROTECTIVE SMARTPHONE CASE

CROSS-REFERENCE TO RELATED APPLICATIONS

This application is a continuation of, claims priority to and the benefit of, U.S. Ser. No. 13/717,969 filed Dec. 18, 2012, now U.S. Pat. No. 9,642,563, and entitled "GLUCOSE MONITORING DEVICE IN A PROTECTIVE SMARTPHONE CASE," which is hereby incorporated by reference in its entirety.

FIELD

The present invention relates to smartphone based glucose monitoring and, more particularly, to a protective cover housing a glucose monitor, testing implements and a power source and a smartphone.

BACKGROUND

Diabetes results from the body's failure to produce insulin (type 1 diabetes) or from insulin resistance in which the body fails to properly use insulin (type 2 diabetes). Diabetes is a major health concern Worldwide. According to the National Institute of Health, diabetes affects 25.8 million people of all ages, or 8.3%, of the U.S. population. This represents approximately 18.8 million diagnosed people and seven million undiagnosed people. It is the seventh leading cause of death in the United States.

To effectively manage and/or control the disease, diabetics must closely monitor and manage their blood glucose levels through exercise, diet and medications in addition to supplying their body with appropriate amounts of insulin based on daily routines. As a result, glucose monitoring systems have become well known in the medical arts. (Other conditions besides diabetes also require monitoring through blood, saliva and urine. Non-limiting examples include low or high hormone levels and hypercholesterolemia.)

Over the years many monitoring systems have been introduced. With these systems, a diabetic typically pricks his or her finger using a lancet. A droplet of exposed blood is applied to a sensor on a test strip which is placed in a glucose monitoring device. A reading appears on a display of the device indicating the blood glucose level of the diabetic.

More recently, advances in technology have led to more sophisticated monitoring. For example, continuous glucose monitoring systems have been developed utilizing sensor technologies incorporating both implantable and external sensors. Other systems deliver the preciseness of finger stick measurements coupled with the convenience of not having to repeatedly prick the skin to obtain glucose measurements.

With the advent of smartphone technology, advances that enable diabetics to record and store monitoring information are now available. More recently, smartphone technology has enabled the user to send recorded information to a remote site, such as a physician. These devices work by plugging a monitoring device into a receptacle on the smartphone and through a software application receive information from the monitor to the smartphone. A drawback to this technology is that the monitor cannot be used with a smartphone in a protective case as the monitor cannot be attached to the phone with the case in place. To use the device, the user must either not use a smartphone protective cover or must remove the protective cover in order to use the monitor. Additionally, if the user desires to leave the monitor attached to the phone, no cover can be used, which thereby exposes both the phone and the monitor to a risk of damage. Moreover, some of these devices force a user to rely on the power of the phone to function. This causes unnecessary battery use which depletes the power for phone use and, importantly, the monitor, which, in turn, can cause a dangerous situation if blood levels cannot be tested at critical times.

Additionally, with other devices a user must carry lancets, a "poking" device, and testing strips separately from the device itself. Thus the overall effect is a bulky package. Moreover, once testing is complete, the user is left with biohazard material debris in the form of a used lancet and test strip.

There is need, therefore, for a glucose monitoring system for use with smartphones in which the apparatus provides a protective covering for both the phone and the monitor and wherein the monitor is powered separately from the phone. Further, there is need for a device that also contains lancets and test strips within the apparatus and there is a receptacle for medical waste. The present invention provides such a device in a convenient to use, hand held protective cover.

OBJECTS OF THE INVENTION

It is an object of the present invention to provide a protective cover that houses both a smartphone and a glucose monitor.

It is a further object of the present invention to further provide a self-contained unit wherein lancets and test strips are housed within the protective cover.

It is a further object of the invention to provide an apparatus containing a lancet striker, or poker.

It is yet another object of the present invention to provide a protective cover that includes a receptacle for debris disposal.

It is yet another object of the present invention to provide a protective cover that includes a power source for the monitor separate from that of the smartphone.

It is yet another object of the present invention to provide a protective cover that can be used with any smartphone and smartphone enabled monitoring device.

SUMMARY

The above objects of the invention are provided for in a novel smartphone protective cover that further houses a glucose monitor, test strips, lancets, a lancet striker, a power source, and a biohazard debris receptacle. According to the invention, the protective covering is a two-piece device having a top portion and a bottom portion. The bottom portion contains a smartphone adaptable glucose monitor. The protective covering is further sized to accept a smartphone, wherein the smartphone is reversibly placed into the bottom portion of the protective covering with the glucose monitor preferably connecting to a data receptacle on the smartphone. In alternate embodiments, the monitor may be a separate unit which is not attached to the smartphone. The top portion of the protective covering is then slid over the smartphone and joined to the bottom portion.

The protective covering has a back side, the back side further including a lancet storage compartment adjacent to a lancet striker having a tension control member and striker release button, test strip storage compartment, and a biohazard debris receptacle. The lancet storage compartment and test strip storage compartment can be re-fillable or disposable. A battery is also located in the back and is electrically connected to the glucose for monitor, thus enabling the monitor to be powered independently of the phone. In other embodiments, the glucose monitor may also be powered by the smartphone or an external battery (rechargeable or static).

While the preferred embodiment is directed to a glucose monitor system, other blood constituents which can be measured by a blood sample are contemplated by the invention.

To use the device, a user removes a test strip from the test strip storage compartment and places it into the glucose monitor, thereby activating the monitor. A lancet is then removed from the lancet storage compartment and placed into the striker chamber. The user then adjusts or reconfirms the striker tension and, when proper tension is chosen, releases the striker by pressing the lancet release button thereby causing the lancet to strike the user's skin causing a blood draw. Blood is then applied to the test strip and the monitor returns a reading. The lancet and test strip are then placed in the biohazard debris receptacle for later disposal.

BRIEF DESCRIPTION OF THE DRAWINGS

FIG. 1 is a front view of the inventive device wherein a phone is positioned within the device and further illustrating the glucose monitor.

FIG. 2 illustrates a back perspective view of the inventive device wherein the protective cover is shown in two parts with a smartphone ready for insertion.

DETAILED DESCRIPTION

Figure 3:
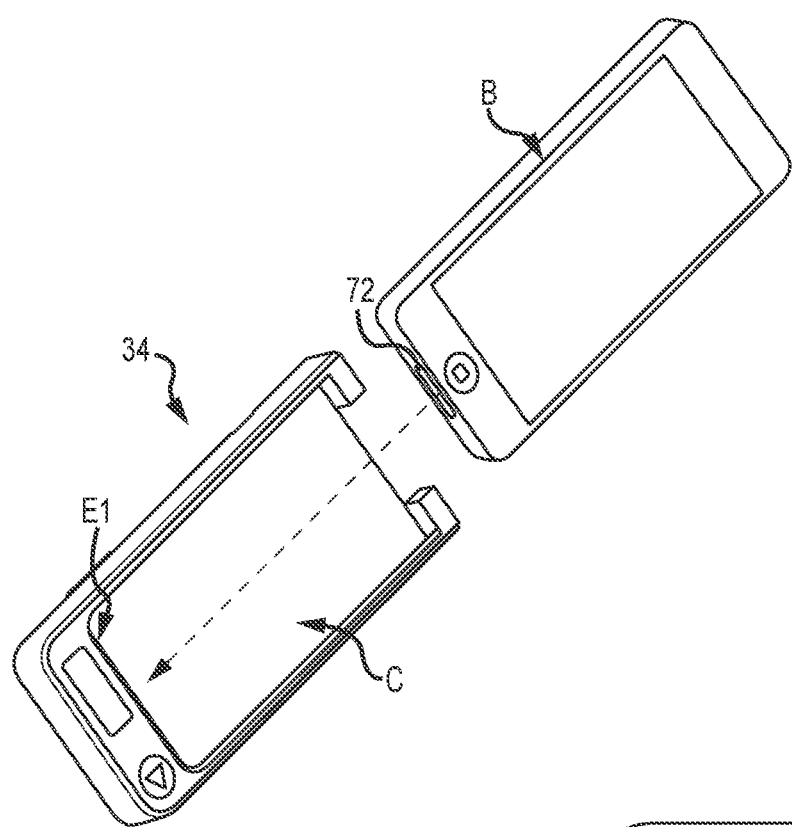
FIG. 3 is a front view of the bottom portion of the inventive device and a smartphone ready for insertion into the bottom portion.

Before explaining the preferred embodiment of the present invention in detail, it is to be understood that the present invention is not limited in its application to the details of arrangements of the components set forth in the following description. As will be appreciated by those skilled in the arts, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention and for examples, they are approximate ranges and are not to be limiting except where noted otherwise.

Unless defined otherwise, all technical and scientific terms used herein have the same meaning as commonly understood by one of ordinary skill in the art to which this invention belongs. Moreover, the singular forms "a", "an", and "the" include plural referents unless the context clearly dictates otherwise.

Importantly, while the present invention is described with reference to a glucose monitor, those skilled in the arts will appreciate that the invention is also applicable to other blood measurable constituents including, but not limited to, cholesterol, low density lipoproteins, very tow density lipoproteins, high density lipoproteins, triglycerides, hemoglobin a1c, C-reactive protein, insulin, human growth hormone, estradiol, progesterone, testosterone, sex hormone binding protein, DHEA-S, thyroid stimulating hormone, T3, T4, thyroid peroxidase antibody, prostate stimulating hormone, luteinizing hormone, and follicle stimulating hormone. The disclosure is meant to encompass these as well as all other measurable blood constituents. Additionally, other types of testing and/or monitors may be used, such as those used for testing saliva or urine. In those cases, the lancet portion of the invention would not be employed. Accordingly, whenever the phrase "glucose monitor" is used, it includes all other smartphone adaptable types of monitoring devices as well.

It should also be understood that the inventive device may include any of the features and respective hardware components described, or combinations thereof, however some features and components may make more practical sense for one particular use, depending on the particular design considerations and intended use, e.g., blood based monitoring versus saliva.

The disclosure uses, for example purposes only, an iPhone (by Apple, Inc., Cupertino, Calif.). Those skilled in the arts will quickly understand that the cover may have a variety of shapes depending on particular design considerations. For example, its general shape will be dictated by the particular model of smartphone, including its overall shape as well as its connection and port placements. The device may be configured to allow the user to use and interact with any input elements and/or graphical displays. In general, however, the cover may be form fitted to a slim rectangular design.

The present disclosure provides an inventive smartphone protective cover (hereinafter also referred to as "cover") comprising a bottom portion and a top portion. In the preferred embodiment, the bottom portion further comprises a glucose monitor (or "tester"). The glucose monitor preferably removably attaches to the data/power port of the smartphone, thereby enabling it to transmit test data to the phone and, from there, either store it or transmit it to a remote location for review or storage. Alternatively, the glucose monitor may be an independent unit that does not attach to the smartphone. In that instance, the glucose monitor is positioned into the bottom portion before cover use. The top portion of the cover is configured to reversibly join the bottom portion at a physical interface. In yet another embodiment, a user may wish to carry a monitor separate from the inventive device, in which case the inventive device is configured to have no space for a monitor but inside is configured to carry the other features of the inventive device.

The cover is sized and shaped to fit one or more external dimensions of a smartphone, while providing access to one or more features of the smartphone, e.g., input units, displays, speakers, microphones, headphone jacks, cameras, communication ports, etc. For example, a cover may be configured to cover greater than greater than 50%, greater than 60%, greater than 70%, greater than 80% or greater than 90% of the exposed surface of a smartphone, depending on the design of the smartphone.

The cover further comprises a back side. The cover back side houses the further inventive elements of the invention, including a lancet storage compartment, a test strip storage compartment, a biohazard material receptacle, a lancet striker, a lancet striker tension adjuster, a lancet striker release button, and a battery compartment. The lancet storage compartment, test strip storage compartment, and biohazard receptacle are removably coupled (throughout, reference to "coupled" means that two modules are currently coupled but are releasably coupled) to the cover back via corresponding recesses located in the cover back adapted to receive each compartment. The Inventors contemplate that the lancet storage compartment, test strip storage compartment, and biohazard receptacle can be reloaded (or emptied in the case of the biohazard material receptacle) or disposed of and replaced with fresh units.

The lancet striker further includes a striker lid, lancet chamber with striker piston, an aperture, and sliding door. The striker lid is a hinged member that, when opened, exposes the striker lancet chamber. The sliding door, when in an opened position, exposes the aperture, through which the lancet tip extends when released. The lancet striker tension adjuster enables the user to regulate the amount of force with which the lancet strikes the skin when the striker piston is released by activating the striker release button.

The biohazard material receptacle is designed to accept used lancets and test strips for later disposal. The glucose monitor is preferably powered by a battery; this feature allows the glucose monitor to run under power independently of the smartphone, thereby saving phone power. The battery is housed in the battery compartment and is electrically connected to the glucose monitor. In other embodiments, the glucose monitor can be powered by the smartphone through a powered connection or through an external battery.

Turning to FIG. 1 inventive device protective cover 20 is seen from the front 22. Cover 20 has a top edge 24, a bottom edge 26, a first side 28, and a second side 30. Cover 20 further comprises two pieces, a top portion 32 and a bottom portion 34. Top portion 32 and a bottom portion 34 join together at physical interface 36. Top portion and bottom portion releasably engage with one another to form a single unit at physical interface 36.

Figure 14:
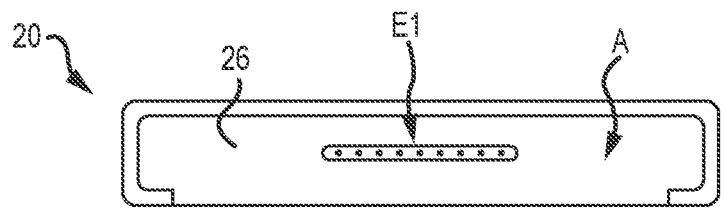
FIG. 14 depicts a top view of the protective cover illustrating the glucose monitor attachment means for connecting to a smartphone.
Figure 15:
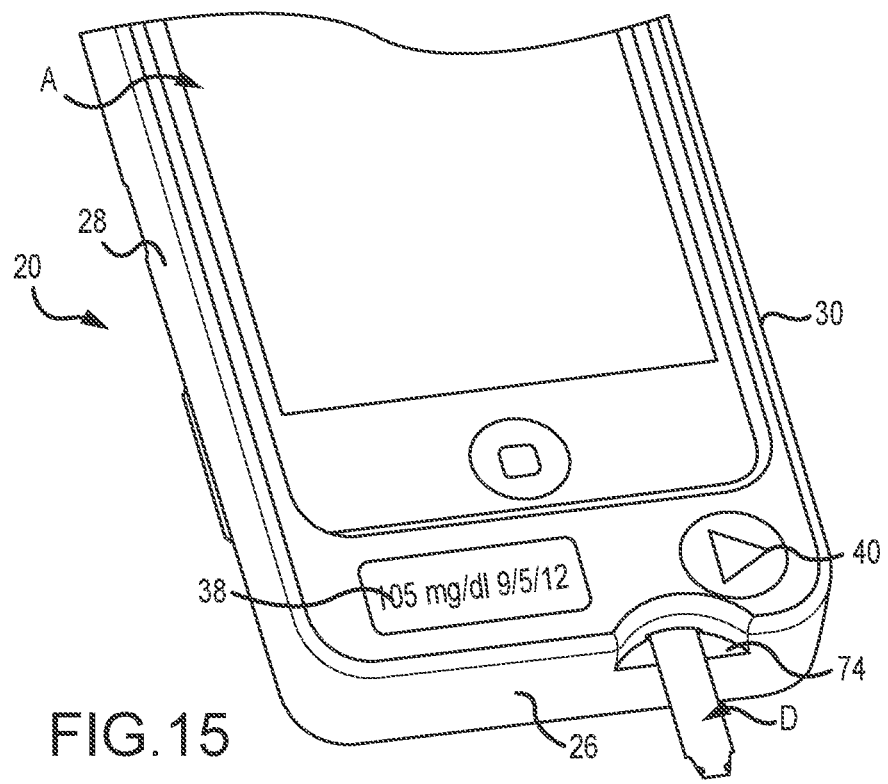
FIG. 15 illustrates a test strip being put into a glucose monitor slot for testing.

Further, bottom portion 34 houses glucose monitor A (depicted in FIG. 14). In the preferred embodiment, the glucose monitor is built-in into the bottom portion and further includes an opening 35 wherein the glucose monitor menu and result screen 38 is exposed and a menu guide selector 40, the menu guide selector enabling a user to scroll through the various options provided by the glucose monitor. Alternatively, bottom portion 34 may not include a built-in glucose monitor and, in that case, is configured to fit over a separate smartphone enabled glucose monitor. Also seen in FIG. 1 is smartphone B exposed through an opening in the front 22 of cover 20.

As will be appreciated by those skilled in the arts, cover 20 can be made of any material that provides protection to the glucose monitor and smartphone and is stiff enough to connect and hold top portion 32 and bottom portion 34 securely in place at physical interface 36. The preferred embodiment contemplates the use of an ABS plastic but any material that provides protection and can connect the top portion and bottom portion together and retain the compartments (described below) is suitable. For non-limiting example, cover 20 can be made of silicone with the addition of a hard plastic piece adjacent physical interface 36 and compartment connections.

In FIG. 2 cover 20 is seen from a back perspective illustrating cover 20 in two parts with smartphone B ready for insertion. As can be seen more clearly in FIG. 3, smartphone B slides into bottom portion 34 along path C with smartphone data transmitter/power hookup 72 (FIG. 3) engaging glucose monitor connector E1 (FIG. 14). Returning to FIG. 2, top portion 32 is then slid over smartphone B and, as shown in FIG. 1 connects at physical interface 36 to bottom portion 34.

As depicted in FIG. 2, connector 42 secures the top portion and bottom portion together by releasably snapping top portion and bottom portion together with bottom portion with connector receivers in bottom portion (not shown). This connection at physical interface 36 is for illustration purposes only and, as those skilled in the arts will understand, there are a number of methods and mechanisms that can secure bottom portion 34 and top portion 32 to one another. The only requirement is that the top portion and bottom portion are securely and reversibly connected to one another. In this non-limiting example of a connection at physical interface 36, to remove top portion 32 from bottom portion 34, the user applies sufficient force to overcome connector 42 from being engaged in the connector receivers (not shown) of bottom portion 34, thus releasing top portion 32 from the connector receivers of bottom portion 34. Other types of connection at physical interface 36 may include, without limitation, a groove and lip connection or a compression fitting.

Figure 4:
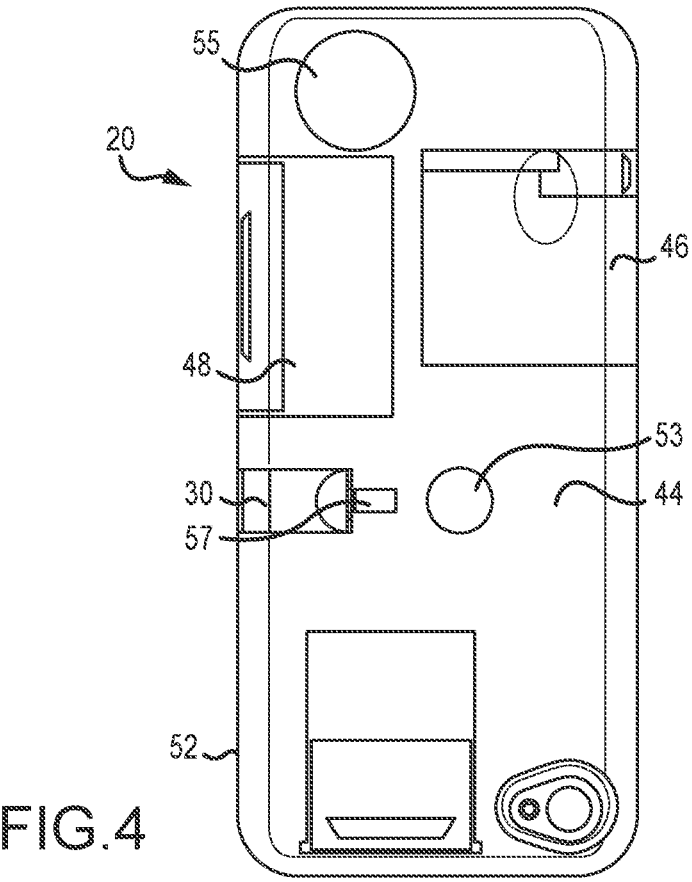
FIG. 4 is a view of the back of the inventive device showing the lancet storage compartment, lancet striker, test strip storage compartment, lancet release button, battery compartment, and biohazard material receptacle.
Figure 5:
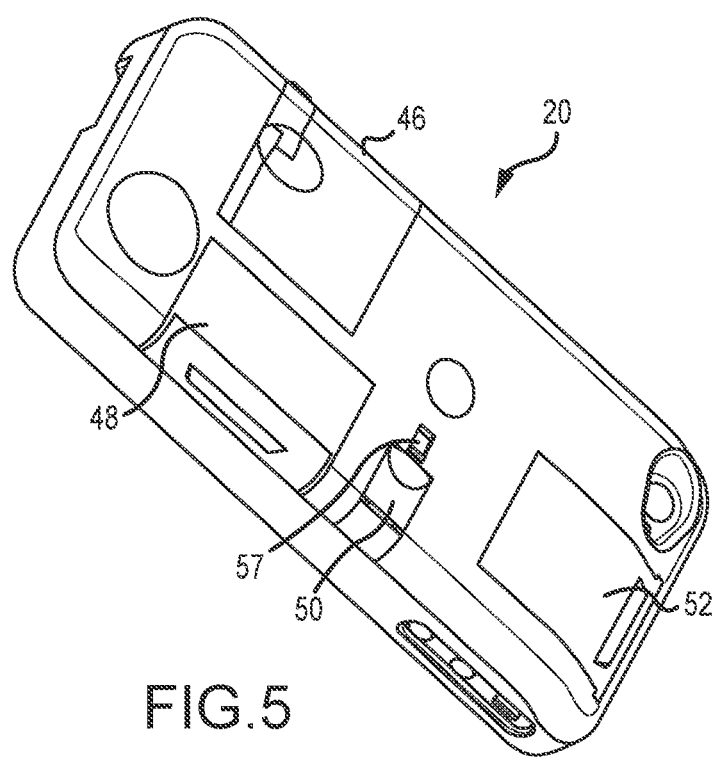
FIG. 5 is a perspective view of the back of the inventive device showing the lancet storage compartment, lancet striker, test strip storage compartment, lancet release button, battery compartment, and biohazard material receptacle.

Turning to FIG. 4 and FIG. 5 cover 20 is seen from cover back 44. Back 44 contains compartments that contain the tools required to perform a test, including test strip storage compartment 46, lancet storage compartment 48, lancet striker 50, biohazard material receptacle 52, striker release 53, and battery compartment 55.

Figure 6:
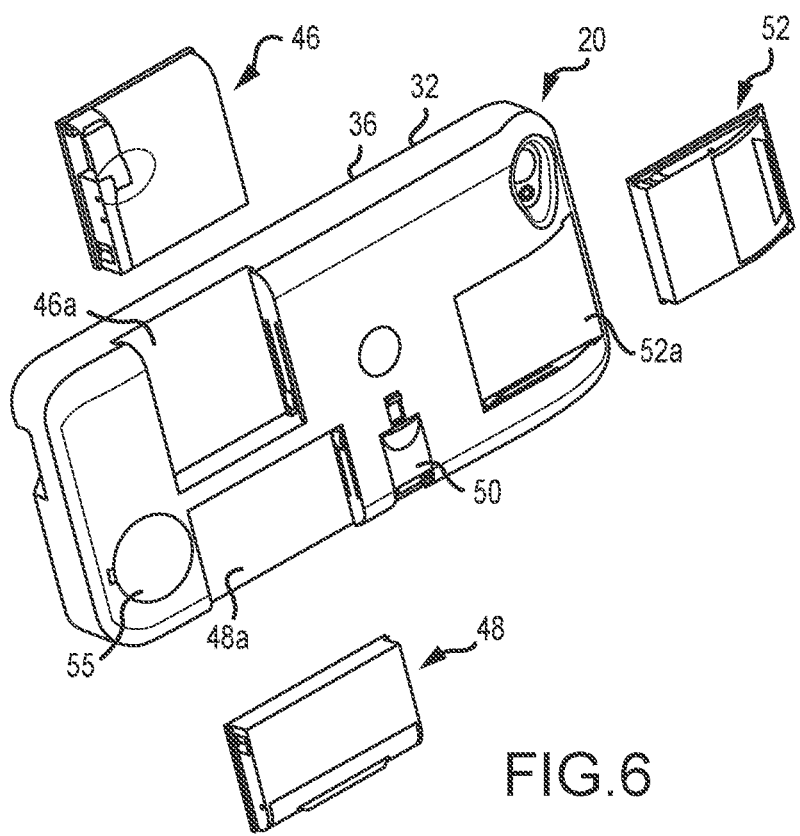
FIG. 6 is an exploded perspective view of the inventive device illustrating the test strip storage compartment, lancet storage compartment, and biohazard material receptacle as a separates units from the protective cover.

FIG. 6 demonstrates that test strip storage compartment 46, lancet storage compartment 48, and biohazard material receptacle 52 are separate units that can be detached from cover 20. The inventors have found that having separate units enables a user to more easily reload test strips and lancets and empty biohazard material. This configuration further enables a user to have either multiple compartments for reloading or, alternatively, the compartments may be disposable and merely replaced when empty (or full in the case of the biohazard material receptacle). However, having separate units is not critical to the invention; having built-in compartments and containers will also work. In the preferred embodiment, which includes separate compartments, each of them slide into receiving recesses 46*a*, 48*a* and 52*a*, respectively to test strip storage compartment 46, lancet storage compartment 48, and biohazard material receptacle 52.

Figure 7:
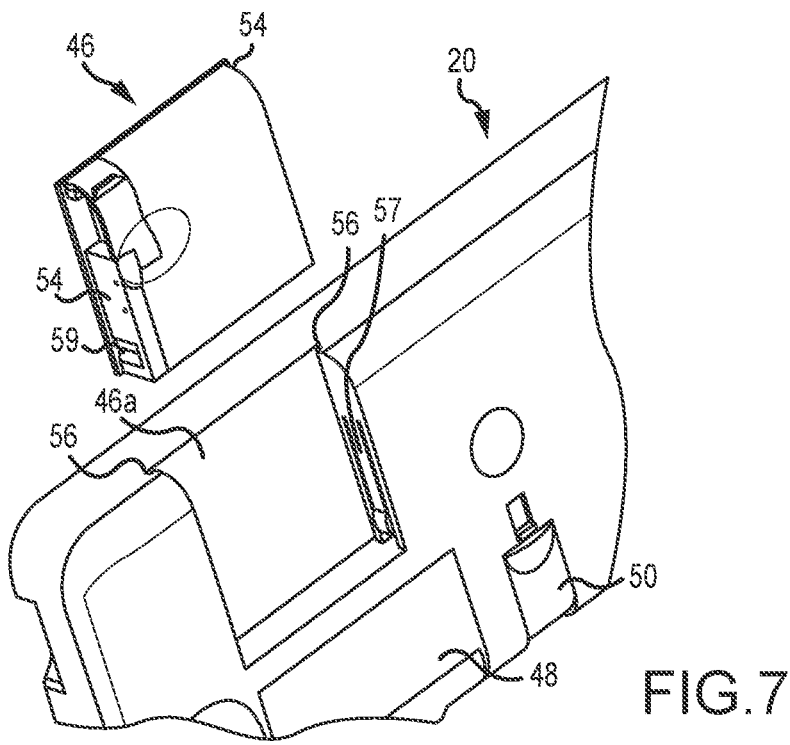
FIG. 7 depicts the test strip storage compartment separate from the protective cover and illustrating attachment system.

FIG. 7 provides a closer and representative view as to how each unit relates to cover 20 by using the test strip compartment for illustration purposes. As can be seen, test strip storage compartment 46 is a self-contained unit that slides into place into recess 46*a* with protrusions 54 sliding along protrusion recess 56. Protrusions 54 of test strip storage compartment 46 are inserted into protrusion recess 56 of cover 20. Recesses 56 are shown as grooves which allow protrusions 54 to slide, permitting the physical interface of lancet storage test strip compartment 46 to slide along the physical interface of recess 46*a*. When test strip storage compartment 46 is slid completely along the sliding plane of recess 46*a*, it "snaps" into a reversibly fixed position via snap hook 57 at test strip compartment 46 hook receiver 59, thus preventing test strip storage compartment 46 from sliding backwards and becoming uncoupled. Each of the other units, the lancet storage compartment 48 and biohazard material receptacle 52, affix and separate in similar fashion. The foregoing compartment coupling explanation is for illustration purposes only and, as those skilled in the arts will understand, there are a number of methods and mechanisms that can secure the compartments, including those explained for use at the physical interface of the top portion and the bottom portion as well as magnetic or hook and loop material.

Figure 8:
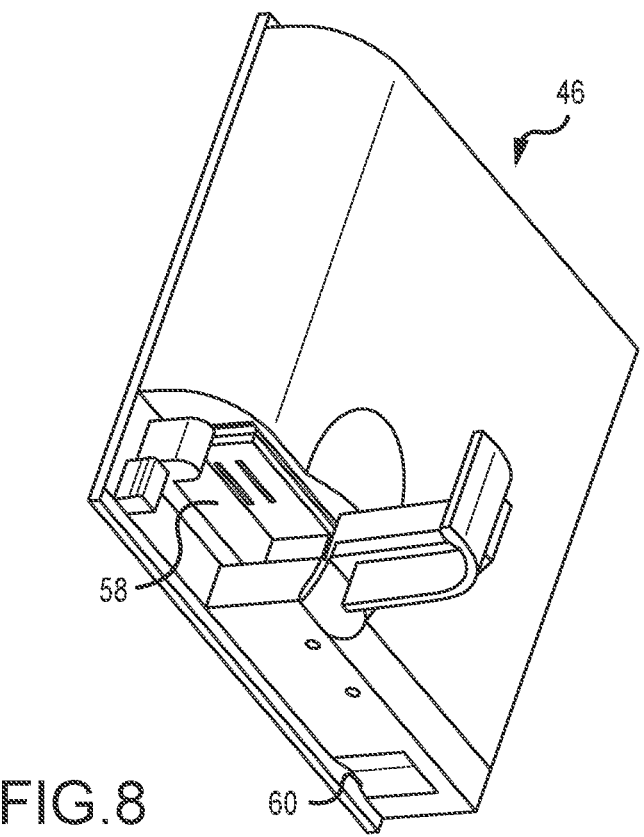
FIG. 8 depicts the test strip storage unit with closure open and exposing the test strip storage receptacle.
Figure 9:
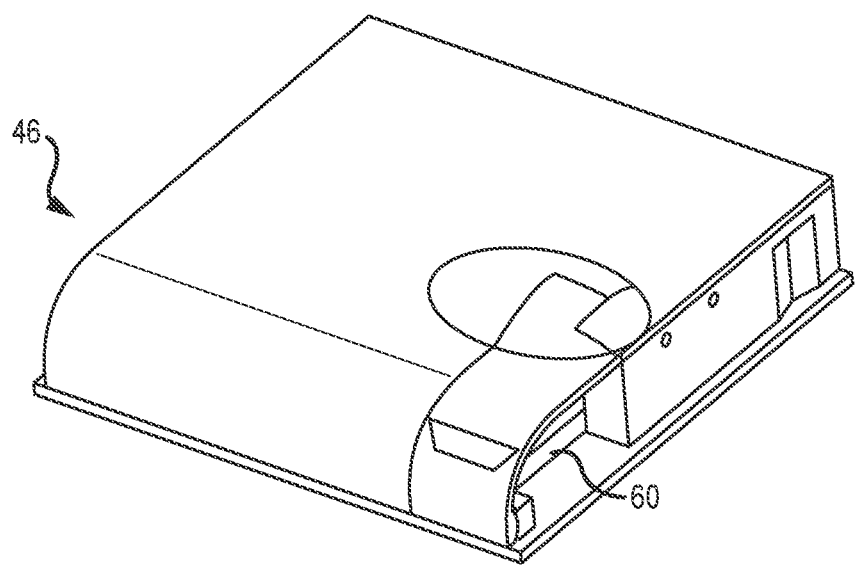
FIG. 9 depicts the test strip storage unit with closure in the closed position, securing test strips in the test strip storage receptacle.

Turning to FIG. 8 another view of test strip storage compartment 46 is seen. In this view, test strip receptacle 58 and closure 60 are depicted. Test strips are load into test strip receptacle 58 and secured into place with closure 60. FIG. 9 illustrates closure 60 in a closed position. Closure 60 is preferably a hinged member but as those skilled in the arts will understand, other closing methods can be employed. For non-limiting example, a sliding mechanism could be used that performs in much the same way as illustrated for test strip storage compartment 46, above.

Figure 10:
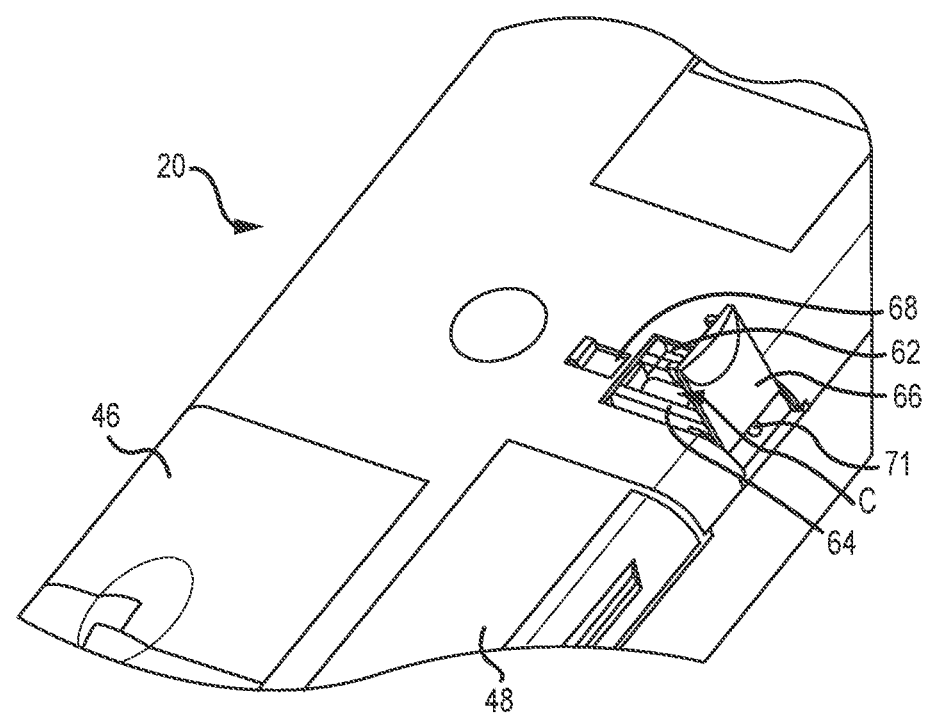
FIG. 10 depicts the lancet striker compartment with the closure open and displaying a lancet.
Figure 11:
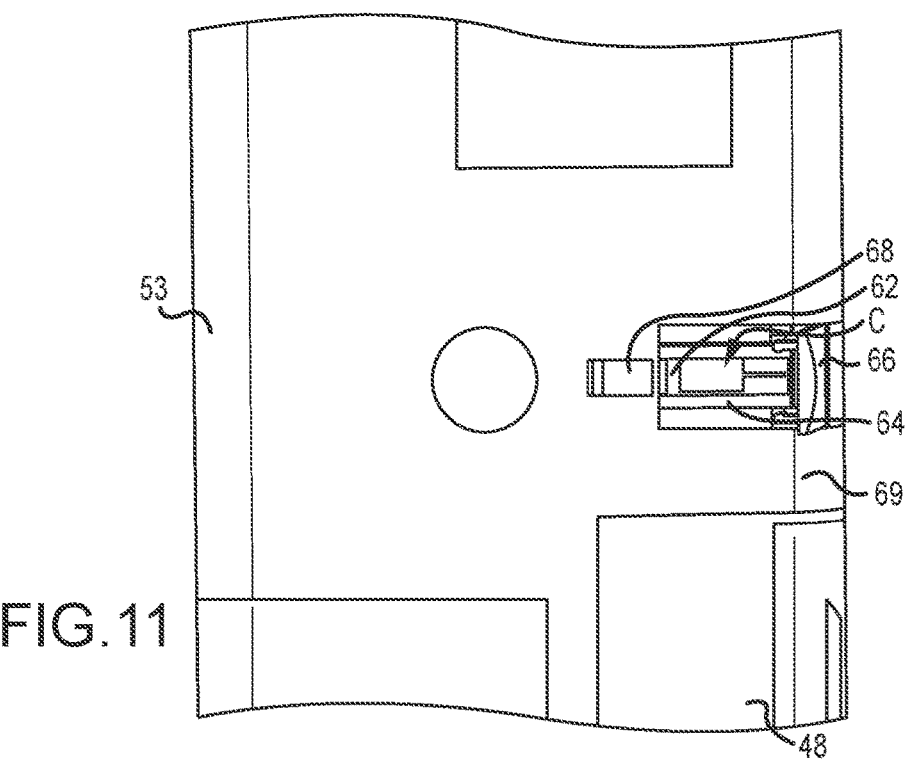
FIG. 11 depicts the lancet striker compartment with the closure open and displaying a lancet.
Figure 12:
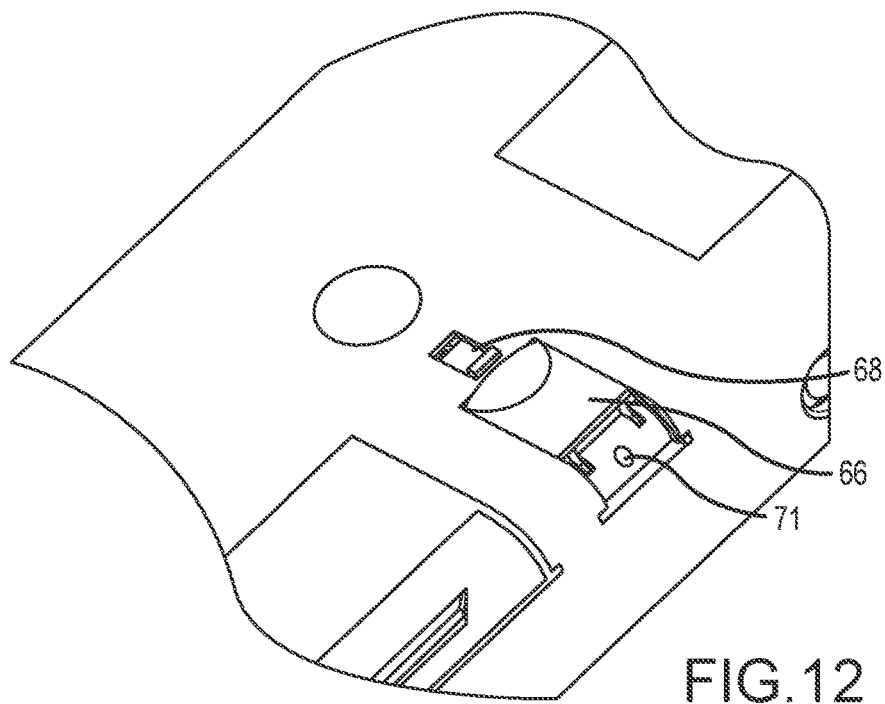
FIG. 12 depicts the lancet striker compartment with the closure closed and dial for striker tension adjustment.
Figure 13:
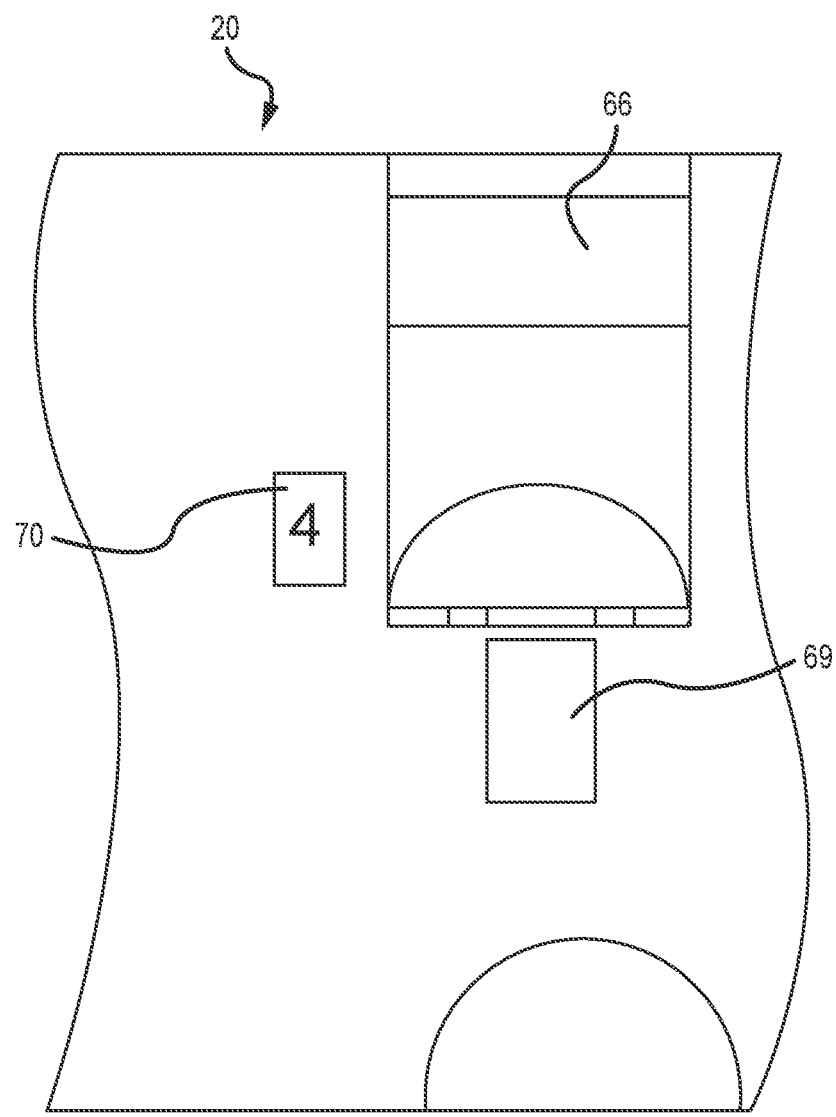
FIG. 13 depicts the lancet striker compartment and striker tension adjustor.

Turning to FIG. 10 and FIG. 11 lancet striker 62 can be seen. Lancet striker 62 accepts lancets C. To insert lancet C into lancet chamber 64, lancet striker closure 66 is opened by pressing striker closure release button 69 and Lancet C is set into position by retracting striker piston 68 via backward pressure on lancet C. Lancet striker closure 66 is then closed (FIG. 12). FIG. 13 illustrates tension adjustor 70 which enables a user to adjust the force that the lancet will strike the skin in order to draw blood during testing. When lancet release button 53 is activated, lancet C is thrust forward through aperture 71, thereby enabling it to strike the skin.

Returning to FIG. 6, battery compartment 55 is shown. The battery compartment houses a battery for supplying power to the glucose monitor. The battery is preferably a watch style, flat battery which is electrically connected to the glucose monitor (circuitry and battery/monitor connection not shown). Its circuitry will vary depending on the style of smartphone and cover configuration. While the preferred embodiment contemplates the use of a watch style battery, other battery types may be used as well, including cylindrical and rechargeable batteries. Further, the glucose monitor could be powered by en external battery housed separately or within the monitor itself. Further, the inventors contemplate that the glucose monitor could be powered by the smartphone via the monitor's connection to the smartphone data/power port.

Figure 16:
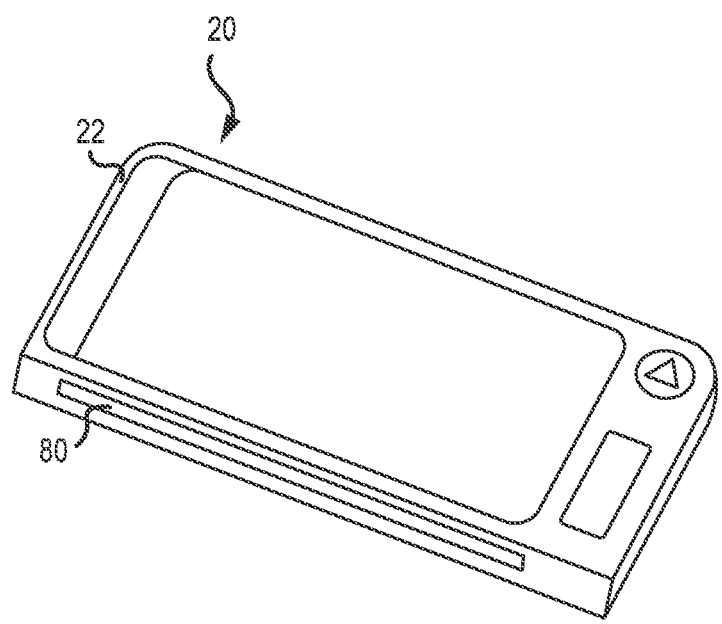
FIG. 16 illustrates an alternate embodiment wherein an insulin shot container is optionally included in the inventive device depicting a groove along one side of the protective cover.
Figure 17:
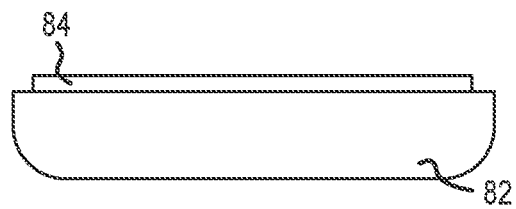
FIG. 17 illustrates an alternate embodiment wherein an insulin shot container is optionally included in the inventive device depicting the container.
Figure 18:
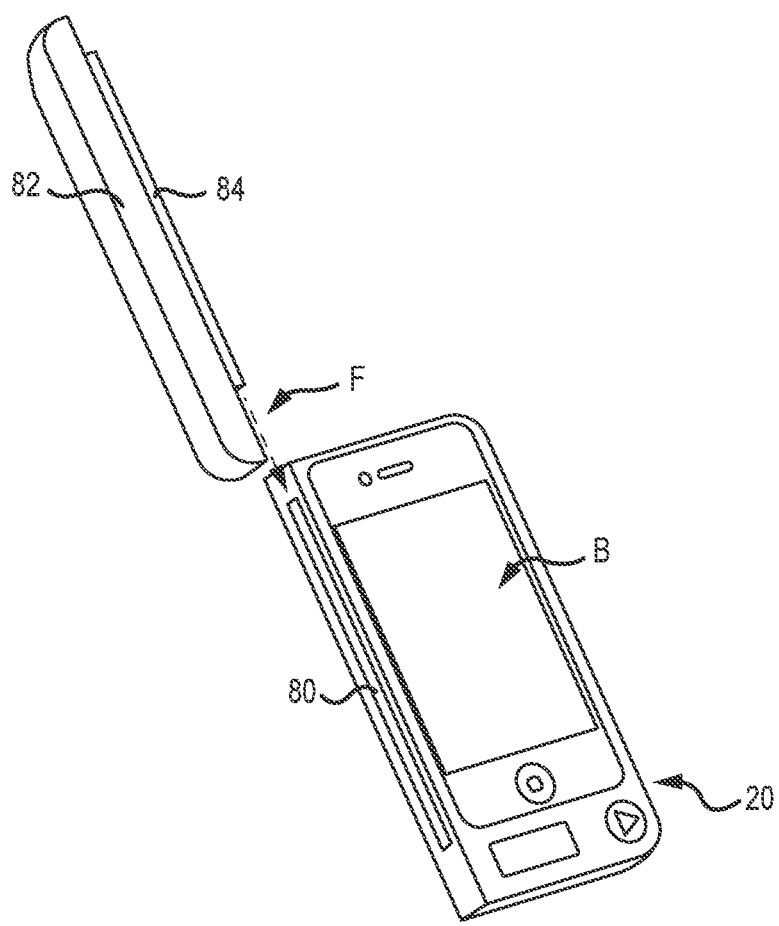
FIG. 18 illustrates an alternate embodiment wherein an insulin shot compartment is optionally included in the inventive device depicting the container being placed into the groove.
Figure 19:
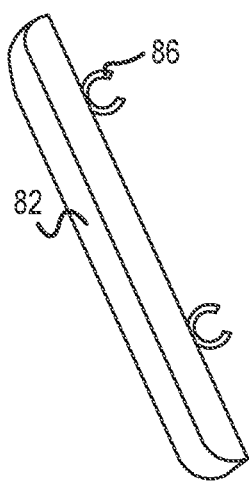
FIG. 19 illustrates an alternate embodiment wherein insulin shot compartment is optionally included in the inventive device depicting an alternate design for the container wherein clasps are used to secure the container to the cover.

In an alternate embodiment, cover 20 will also include a general storage compartment for holding items, such as insulin shots. In this embodiment, cover 20 will include a groove 80 along the length of one of its sides (FIG. 16). As seen in FIG. 17, Container 82 includes a lip 84 that is inserted into groove 80 (as depicted in FIG. 18) and slid along the length of the groove along path F. Container 82 is a hollow canister that can be of any suitable shape, e.g., cylindrical, square, rectangular. It is desirable that container 82 be of a size relative to the thickness of cover 20 but this is not critical. In yet another embodiment, and with reference to FIG. 19, container 82 may have clasps 86 that secure the container to cover 20 by friction.

To use the device a user will first put it in functional order. To do this, a user has the option to load the compartments and place them into the recesses of the cover before loading a smartphone into the cover or loading the smartphone into the cover and then loading the compartments. There is no preferred order. In the instance where a user loads the smartphone first, the user slides a smartphone into the bottom portion of the cover 34, engaging the smartphone data transmitter/power hookup 72 with glucose monitor A data transmitter/power adaptor E. The connection between the glucose monitor and the smartphone enables data collected by the glucose monitor to be transmitted to the smartphone where it can alternatively or collectively be displayed on the smartphone screen, stored locally in the smartphone, or be transmitted to a remote location for storage or review. Top portion 32 is then slid over smartphone B until connection is made to bottom portion 34 at physical interface 36. Cover 20 is then in place and serves to protect both the smartphone and the glucose monitor. The user then loads the compartments into the recesses of the cover by placing protrusions 54 of a selected compartment, for example lancet storage compartment 48 into protrusion recess of cover and sliding the compartment along the physical interface of the recess. When the compartment is slid completely along the sliding plane of recess, it "snaps" into a reversibly fixed position via snap hook 57. Each of the other units affix and separate in similar fashion. To remove a compartment, sufficient pressure is applied to the compartment in a direction opposite to that used when loading the compartment. The compartment may then be replaced or reloaded as selected by the user.

In the instance where the compartments are loaded first, the processes described above are reversed: the compartments are loaded and then the smartphone is placed into the cover.

In another embodiment where the glucose monitor is not built into the cover, the user, instead of engaging the smartphone data transmitter/power hookup with glucose monitor data transmitter/power adaptor, would place a glucose monitor into the bottom portion of the cover. The user would then slide a smartphone into the bottom portion 34 of the cover 20 until such point that it lays adjacent the glucose monitor. Top portion 32 is then slid over smartphone B until connection is made to bottom portion 34 at physical interface 36. Cover 20 is then in place and serves to protect both the smartphone and the glucose monitor.

To use the inventive device, a user removes a test strip from the test strip storage compartment and places it into the glucose monitor, thereby activating the glucose monitor. The user then removes a lancet from the lancet storage compartment and positions it into lancet striker chamber of the lancet striker. The user adjusts or reconfirms the striker tension with tension adjustor and, when proper tension is chosen, presses the lancet release button causing the lancet to strike the user's skin causing a blood draw. The user then smears the test strip with blood. A reading is taken, displayed screen 38, and, if so desired, transmitted to smartphone B where it can be recorded, stored, or sent to a desired location. The glucose monitor may provide a variety of menus, selections, charts, alarms, reminders, visual indicators, etc. For example, the user may be presented with menus and options, such as whether to take a measurement reading, to view stored measurement readings, to store data, to download data, to perform bolus calculation based on the measurement, etc.

The lancet and test strip are then placed in biohazard material receptacle 52.

The foregoing describes the preferred embodiment during operation in use as a glucose monitor. It should be understood that the description applies equally to other analytes and to other forms of samples involving a blood draw. In the instance where a different type of sample is used (e.g., saliva), the steps involving the lancet, obviously, would not be required.

Importantly, while the invention has been described with reference to figures showing the invention in a particular configuration, those skilled in the arts will understand that placement of the various features of the device is not critical. For instance, the striker could be placed near top edge 24. Likewise, the location of the various compartments can be altered and may be based upon the design of the smartphone and its ports, speakers, controls, etc.

As will also be understood by those skilled in the arts, the order of the steps of the method described above is not critical. The spirit of the invention and the method for employing it are found in the individual features of the invention and their use, not the order in which they are used or presented herein.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

The invention claimed is:

1. A body fluid monitoring system for use with a smartphone comprising:
   a protective cover comprising a first portion and a second portion, the second portion configured to house a body fluid monitor,
   wherein the first portion and second portion reversibly couple to one another at a physical interface to secure a smartphone between the first portion and second portion, and
   wherein the protective cover further comprises a test strip storage compartment, a power source, and a biohazard material receptacle having a re-sealable opening for storing by a human at least one used test strip and at least one used lancet.

* * * * *